(12) United States Patent
Hunziker et al.

(10) Patent No.: US 7,901,971 B2
(45) Date of Patent: Mar. 8, 2011

(54) METHOD FOR MANUFACTURING A SENSOR DEVICE WITH A STRESS RELIEF LAYER

(75) Inventors: Werner Hunziker, Stäfa (CH); Franziska Brem, Zürich (CH); René Hummel, Stäfa (CH)

(73) Assignee: Sensirion AG, Stafa (CH)

( * ) Notice: Subject to any disclaimer, the term of this patent is extended or adjusted under 35 U.S.C. 154(b) by 23 days.

(21) Appl. No.: 12/462,528

(22) Filed: Aug. 5, 2009

(65) Prior Publication Data

US 2010/0035373 A1 Feb. 11, 2010

(30) Foreign Application Priority Data

Aug. 11, 2008 (EP) .................................. 08014276

(51) Int. Cl.
*H01L 21/00* (2006.01)

(52) U.S. Cl. .................... 438/55; 438/113; 257/E21.599

(58) Field of Classification Search ............ 438/48, 438/54, 55, 113; 257/467, 468, E21.504, 257/E21.599
See application file for complete search history.

(56) References Cited

U.S. PATENT DOCUMENTS

| | | | |
|---|---|---|---|
| 4,888,988 A | 12/1989 | Lee et al. | |
| 4,894,707 A | 1/1990 | Yamawaki et al. | |
| 5,026,667 A * | 6/1991 | Roberts, Jr. ................... | 438/114 |
| 5,332,469 A | 7/1994 | Mastrangelo et al. | |
| 5,863,810 A | 1/1999 | Kaldenberg | |
| 5,897,338 A | 4/1999 | Kaldenberg | |
| 6,379,988 B1 | 4/2002 | Peterson et al. | |
| 6,395,585 B2 | 5/2002 | Brandl | |
| 6,489,178 B2 | 12/2002 | Coyle et al. | |
| 6,613,607 B2 | 9/2003 | Janssen et al. | |
| 6,690,569 B1 | 2/2004 | Mayer et al. | |
| 6,729,181 B2 | 5/2004 | Mayer et al. | |
| 6,750,522 B1 | 6/2004 | Mayer et al. | |
| 7,067,350 B1 * | 6/2006 | Liou ............................. | 438/106 |
| 7,109,574 B2 | 9/2006 | Chiu et al. | |
| 7,154,372 B2 | 12/2006 | Vanha et al. | |
| 7,205,175 B2 | 4/2007 | Raben | |
| 7,312,106 B2 | 12/2007 | Raben | |
| 7,777,352 B2 * | 8/2010 | Mahler et al. ................. | 257/784 |

(Continued)

FOREIGN PATENT DOCUMENTS

DE 19929025 12/2000

(Continued)

OTHER PUBLICATIONS

Search Report for European Application No. 08014276.3, Feb. 9, 2009.

(Continued)

*Primary Examiner* — Tuan N. Quach
(74) *Attorney, Agent, or Firm* — Richard F. Jaworski; Cooper & Dunham LLP

(57) ABSTRACT

A method for packaging a sensor device having a sensitive structure integrated on a semiconductor chip is provided. When molding the device package, an inward extending section of the mold maintains an access opening to the sensor. A buffer layer is arranged on the chip between the inward extending section and the sensitive structure. The buffer layer protects the sensitive structure from damage by the inward extending section and acts as a seal while casting the housing. The buffer layer also covers at least part of the semiconductor electronic components of the circuitry integrated onto the chip. By covering these components, mechanical stress, as it is e.g. caused by different thermal expansion coefficients of the packaging and the chip, can be reduced.

20 Claims, 3 Drawing Sheets

U.S. PATENT DOCUMENTS

| | | |
|---|---|---|
| 2001/0023087 A1 | 9/2001 | Brandl |
| 2003/0115952 A1 | 6/2003 | Mayer et al. |
| 2005/0140005 A1* | 6/2005 | Huang et al. .................. 257/737 |
| 2006/0234414 A1 | 10/2006 | Van Der Wiel |
| 2007/0231942 A1 | 10/2007 | Vanha et al. |
| 2008/0006076 A1 | 1/2008 | Mayer et al. |
| 2008/0258318 A1* | 10/2008 | Kimura .......................... 257/793 |
| 2010/0117185 A1* | 5/2010 | Hunziker et al. ............. 257/467 |

FOREIGN PATENT DOCUMENTS

| | | |
|---|---|---|
| EP | 1211722 | 6/2002 |
| EP | 1220309 | 7/2002 |
| EP | 1465244 | 10/2004 |
| EP | 1873499 | 1/2008 |
| EP | 2154713 | 2/2010 |
| JP | 02227485 | 9/1990 |
| WO | WO0229853 | 4/2002 |
| WO | WO2006114005 | 11/2006 |
| WO | WO2008046235 | 4/2008 |

OTHER PUBLICATIONS

"A Low Cost Wafer-Level MEMS Packaging Technology", Pejman Monajemi et al., IEEE, 2005, pp. 634-637.

Sensor and Actuators A 67 (1998), pp. 185-190, "Low-cost Plastic Sensor Packaging Using the Open-window Package Concept", C. Cotofana et al.

* cited by examiner

METHOD FOR MANUFACTURING A SENSOR DEVICE WITH A STRESS RELIEF LAYER

CROSS REFERENCE TO RELATED APPLICATIONS

This application claims the priority of European patent application 08014276.3, filed Aug. 11, 2008, the disclosure of which is incorporated herein by reference in its entirety.

BACKGROUND OF THE INVENTION

The invention relates to a method for manufacturing a sensor device with a buffer layer.

WO 2006/114005 describes a method for housing a sensor device having a sensitive structure integrated on a semiconductor chip. The device is packaged by transfer molding. During the molding operation, an inward extending section of the mold maintains an access opening to the sensor. A buffer layer is arranged on the chip between the inward extending section and the sensitive structure. The buffer layer protects the sensitive structure from damage by the inward extending section and acts as a seal while casting the housing.

BRIEF SUMMARY OF THE INVENTION

It is an object of the present invention to provide a method of this type that further simplifies the manufacturing process and allows to manufacture accurate devices.

Now, in order to implement these and still further objects of the invention, which will become more readily apparent as the description proceeds, the invention provides a method for manufacturing a sensor device having a chip with an integrated sensitive structure and integrated circuitry, and wherein said circuitry comprises semiconductor electronic components, said method comprising the steps of integrating, onto a surface of said chip, a buffer layer surrounding said sensitive structure, providing a mold defining an interior space and having a section extending into said interior space, placing said chip in said mold with said section abutting against said buffer layer, introducing a hardening material into said mold for casting a housing over said chip, after hardening said material at least partially, removing said section thereby forming an access opening extending to said sensitive structure, wherein said buffer layer covers at least part of said semiconductor electronic components.

In a further aspect, the invention relates to a method for manufacturing a sensor device having a chip with an integrated sensitive structure and integrated circuitry, and wherein said circuitry comprises semiconductor electronic components, said method comprising the steps of providing a wafer comprising a plurality of chips, integrating, onto a surface of said chips, a buffer layer surrounding said sensitive structure, wherein said buffer layer is structured on said wafer by removing said buffer layer at least partially at a location of said sensitive structure, after structuring said buffer layer, cutting said wafer into said chips, providing a mold defining an interior space and having a section extending into said interior space, placing at least one of said chips in said mold with said section abutting against said buffer layer, introducing a hardening material into said mold for casting a housing over said at least one chip, after hardening said material at least partially, removing said section thereby forming an access opening extending to said sensitive structure, wherein said buffer layer covers at least part of said semiconductor electronic components.

A "semiconductor electronic component" is an electronic component exploiting the semiconducting properties of the material. In particular, such components comprise transistors and diodes as well as any further components having pn-junctions or MIS or MOS structures.

A "non-linear" electronic component is a component that shows non-linear voltage-current characteristics under regular operating conditions, such as a diode or a bandgap circuit. Normal resistors or leads, for example, are not considered to be "non-linear" electronic components since, for practical applications, they have linear characteristics under normal operating conditions.

An "active" electronic component is a component showing a gain, in particular a power gain, for an incoming signal, such as an amplifier or a transistor.

Such non-linear and active components generally suffer substantially from mechanical stress in the chip, i.e. their electronic properties change e.g. under strain. By covering them at least in part by the buffer layer, such strain, as it is e.g. caused by different thermal expansion coefficients of the housing and the chip, can be reduced.

Hence, the buffer layer has two functions. On the one hand, while casting the housing, it serves as a seal towards and a protection against the projecting section of the mold as described above. On the other hand, it acts as a stress relief layer between at least part of the semiconductor electronic components, in particular at east part of the non-linear and/or active components, of the integrated circuitry and the housing.

Instead of using a separate stress release layer or no stress release layer at all, the present invention uses the buffer layer as stress release layer and also as a protection and seal during molding, which simplifies the manufacturing process while allowing to manufacture accurate devices.

The buffer layer can advantageously be used to cover transistors, diodes as well as so-called bandgap circuits. A "bandgap circuit" is a circuit generating a voltage depending on the bandgap of the semiconductor material used in the chip. Typical examples of such circuits are reference voltage sources and temperature sensors.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE INVENTION

In the following, an embodiment of the manufacturing process according to the invention is described by reference to FIGS. 1 to 6.

Figure 1:
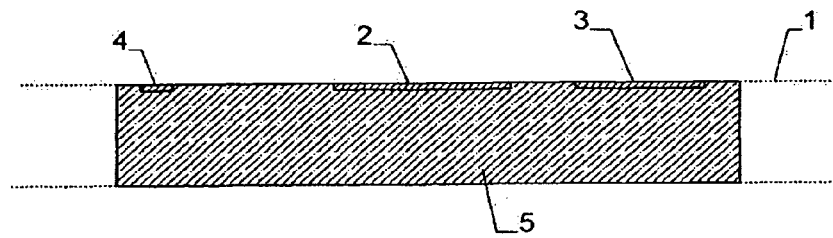
FIG. 1 a first step in a manufacturing process of the sensor, prior to applying the buffer layer, FIG. 2 a second step, after applying the buffer layer, FIG. 3 a third step, after structuring the buffer layer, FIG. 4 a fourth step, after cutting the wafer and applying the chip to the lead frame, FIG. 5 a fifth step prior to casting, FIG. 6 a sixth step, after removing the mold, FIG. 7 a reference voltage generator and temperature sensor.
Figure 2:
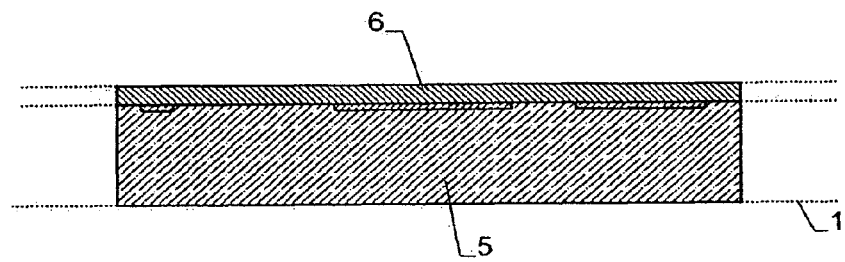

In a first step, a plurality of sensor chips is manufactured simultaneously on a wafer 1. FIG. 1 shows a single chip 5 in detail. Each chip may e.g. be a humidity sensor as it is described in U.S. Pat. No. 6,690,569. Or it may be any other type of sensor having a sensitive structure 2 and electronic circuitry 3 integrated thereon. Sensitive structure 2 may e.g. be the polymer film of a humidity sensor with underlying electrodes as described in U.S. Pat. No. 6,690,569. Circuitry 3 may e.g. comprise analog amplifiers, analog-digital converts and digital processing electronics.

Furthermore, bond pads 4 are provided for connecting circuitry 3 to bond wires.

In a next step, a buffer layer 6 is applied over wafer 1. Advantageously, buffer layer 6 is a photoresist, such as SU-8 by MicroChem Corp., USA. Using a photoresist layer as buffer layer 6 has the advantage that it can be structured easily.

Figure 3:
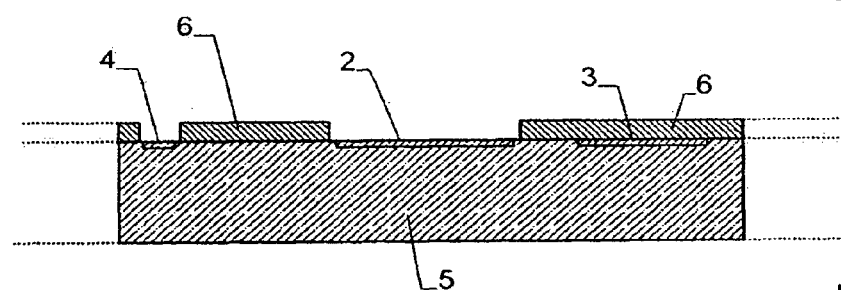

Buffer layer 6 is structured by means of photolithography in order to remove it at least partially at the location of sensitive structure 2 as well as at the location of the bond pads 4, as shown in FIG. 3. All steps up to this point can be carried out prior to cutting wafer 1.

Figure 4:
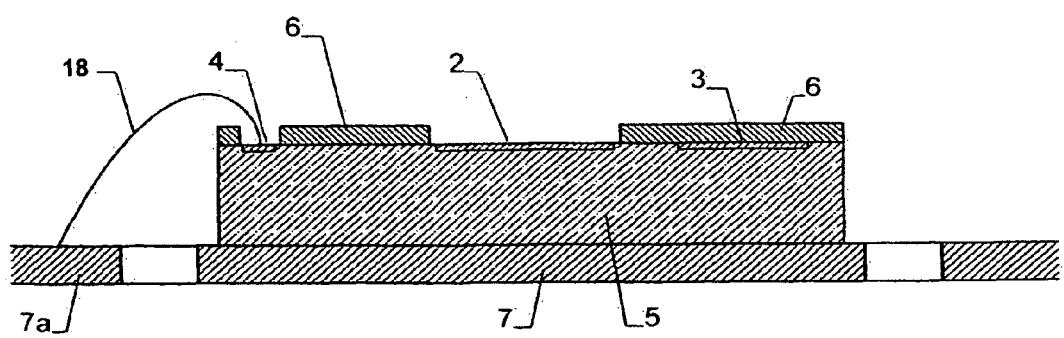

Now, wafer 1 is cut into the chips 5, and a plurality of the chips 5 are placed on a lead frame 7 in known manner, as shown in FIG. 4. The chips 5 may e.g. be glued to the lead frame 7. Bond wires 18 are mounted between the contact pads 4 and the leads 7a of lead frame 7.

In a next step, lead frame 7 is placed in a mold comprising a lid 8 and a base 9. The mold defines an interior space 10 to be filled by a hardening material. Lid 8 has a section 11 that extends into interior space 10. Section 11 is located and dimensioned such that, when the mold is closed, it abuts against buffer layer 6 along a circumference of sensitive structure 2, thereby forming a sealed cavity 12 over sensitive structure 2.

Figure 5:
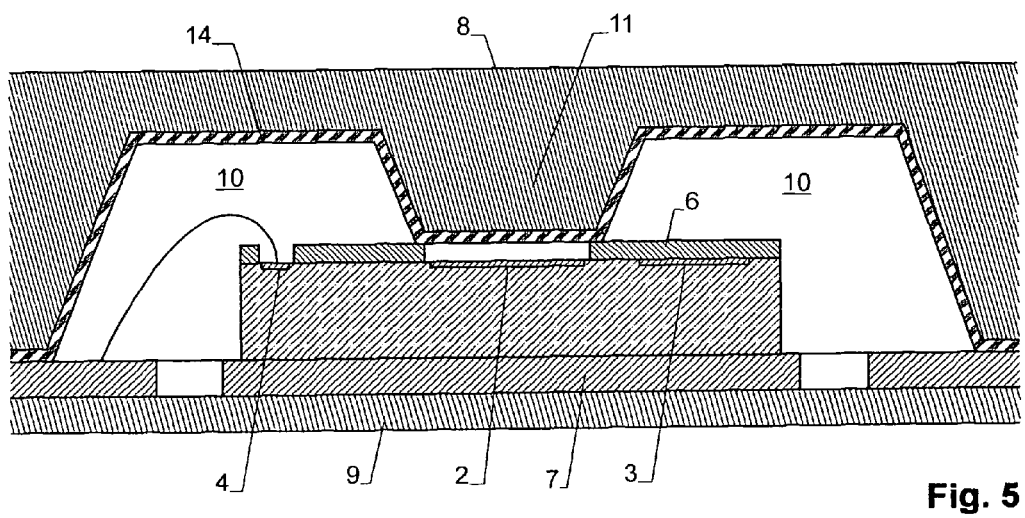

As shown in FIG. 5, a foil assisted molding process can be used. In such a process, a film 14 is placed over at least one of the parts of mold 8, 9 on the side facing interior space 10. Film 14 may e.g. be a ETFE film having a thickness between 50 and 100 μm. A suitable example of such a film is Nowoflon ET6235J by Nowofol, Siegsdorf (Germany) or Fluon by Asahi Glass Co., Japan. Such a foil compensates mechanical tolerances, reduces the wear of the mold and simplifies the removal of the mold after the casting process. Similarly, base 9 can be formed by a polyester foil. A suitable polyester foil is e.g. RM4100 by Hitachi Chemicals, Japan.

In a next step, a hardening material is introduced into the mold to fill interior space 10.

Figure 6:
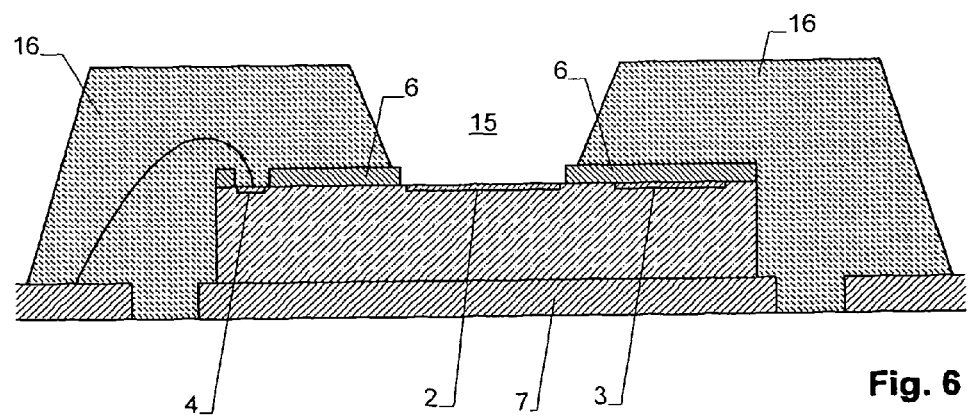

After hardening the material at least partially in order to form a package or housing 16 that covers and/or surrounds chip 5, mold 8, 9 is removed, thereby forming the substantially completed device as shown in FIG. 6. As can be seen, section 11 has formed an access opening 15 that connects sensitive structure 2 with the surroundings of the device.

According to the present invention, buffer layer 6 is formed such that it covers at least part of the semiconductor electronic components of the circuitry 3 in order to protect them from mechanical stress, such as strain.

For providing a good mechanical protection during molding and thereafter, and in order to avoid a damage of sensitive structure 2 during the molding process, buffer layer 6 advantageously has the following properties:

Its height should be sufficient such that film 14 is prevented from touching sensitive structure 2 during the molding process. Advantageously, the height of buffer layer 6 is at least 10 μm.

It should be sufficiently elastic in order to form a good seal during the molding process and in order to be able to accommodate for mutual movements between housing 16 and the circuitry semiconductor chip 5. In particular, it should be more elastic than normal cover layers applied over semiconductor chips, in particular SiN and $SiO_2$. In particular, buffer layer 6 should have a Young's module of less than 10 GPa, which is clearly smaller than the Young's modules of SiN (>150 GPa) and $SiO_2$ (>70 GPa).

Advantageously, buffer layer 6 is (or comprises) a resin system e.g. epoxy, in particular a photostructurable resin system such that it can be structured easily. Resin systems have been found to be compatible with the materials that are usually used for injection-molded semiconductor device packaging.

Alternatively, buffer layer 6 may e.g. also be or comprise a rubber, e.g. silicone rubber, polyimide. If it is not a photoresist, a separate photoresist layer can e.g. be placed on top of it, which then can be structured to form a mask for subsequently etching the buffer layer at the desired locations.

Alternatively, buffer layer 6 may also be applied using printing techniques, such as stencil printing or screen printing, in particular if buffer layer 6 is a silicone rubber.

As mentioned, buffer layer 6 not only serves to provide a seal with section 11 in the molding process, but it also protects at least part of the semiconductor electronic components of circuitry 3 from strain. Advantageously, it is structured such that it covers substantially all of circuitry 3.

This is based on the understanding that mechanical stress strongly affects the properties of semiconductor electronic components, while, at the same time, buffer layer 6 can be used not only as a contact surface for section 11 of the mold, but also as a stress relief layer.

Figure 7:
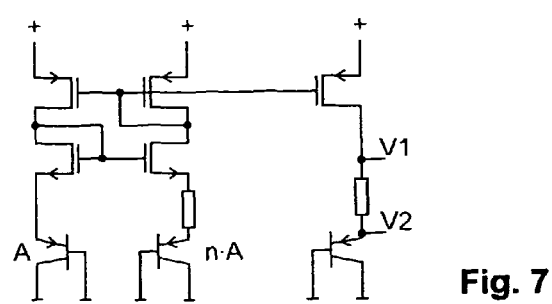
Figure 8:
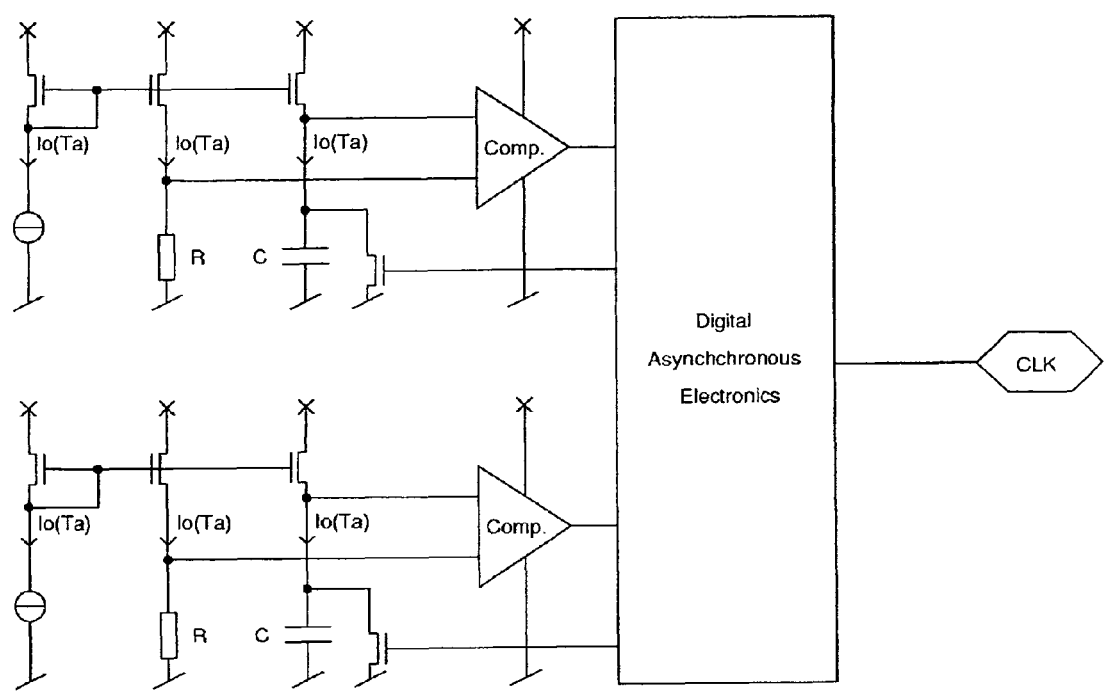
FIG. 8 is an RC oscillator.

Most advantageously, buffer layer 6 is arranged over the following components:

a) transistors and/or diodes b) analog circuitry, such as analog amplifiers—in contrast to digital circuitry, analog circuitry is more prone to change its properties under mechanical strain, c) oscillators—in particular oscillators whose frequency is defined by the properties of the integrated components; this is e.g. the case in ring oscillators as well as RC oscillators; an example for an RC oscillator is shown in FIG. 8, d) band gap circuits, in particular reference voltage generators and temperature sensors—an embodiment of a band gap circuit optimized as reference voltage generator and as a temperature sensor is shown in FIG. 7. A constant reference voltage can be obtained at output V1, while the voltage difference between outputs V1 and V2 is a measure of the temperature.

While there are shown and described presently preferred embodiments of the invention, it is to be distinctly understood that the invention is not limited thereto but may be otherwise variously embodied and practised within the scope of the following claims.

The invention claimed is:

1. A method for manufacturing a sensor device having a chip with an integrated sensitive structure and integrated circuitry, and wherein said circuitry comprises semiconductor electronic components, said method comprising the steps of integrating, onto a surface of said chip, a buffer layer surrounding said sensitive structure, providing a mold defining and interior space and having a section extending into said interior space, placing said chip in said mold with said section abutting against said buffer layer, introducing a hardening material into said mold for casting a housing over said chip, after hardening said material at least partially, removing said section thereby forming an access opening extending to said sensitive structure, wherein said buffer layer covers at least part of said semiconductor electronic components.

2. The method claim 1 wherein said buffer layer covers at least one transistor and/or diode of said integrated circuitry.

3. The method of claim 1 wherein said integrated circuitry comprises analog circuitry and wherein said buffer layer covers at least part of said analog circuitry.

4. The method of claim 3 wherein said buffer layer covers at least an amplifier of said analog circuitry.

5. The method of claim 1 wherein said buffer layer covers at least part of an Oscillator.

6. The method of claim 1 wherein said buffer layer covers at least one band gap circuit.

7. The method of claim 1 wherein said buffer layer covers at least part of a reference voltage generator.

8. The method of claim 1 wherein said buffer layer covers at least part of a temperature sensor.

9. The method of claim 1 wherein said buffer layer has a height of at least 10 μm.

10. The method of claim 1 wherein said buffer layer comprises a resin system.

11. The method of claim 10 wherein said resin is photosensitive and is structured by microlithography.

12. The method of claim 1 wherein said buffer layer comprises a photoresist and is structured by microlithography and/or wherein said buffer layer is applied by a printing technique.

13. The method of claim 12, wherein said printing technique comprises stencil printing or screen printing.

14. The method of claim 1 wherein said buffer layer is more elastic than SiN and $SiO_2$.

15. The method of claim 14, wherein said buffer layer has a Young's module of less than 10 GPa.

16. The method of claim 1 wherein said chip is cut from a wafer and wherein a plurality of said chips are manufactured together on a single wafer, whereupon said wafer is cut into said chips, and wherein said buffer layer is applied to said wafer prior to cutting said wafer.

17. The method of claim 16 wherein said buffer layer is structured on said wafer prior to cutting said wafer by removing said buffer layer at least partially at a location of said sensitive structure.

18. The method of claim 1 wherein said chip is placed on a lead frame and mounted in said mold on said lead frame.

19. The method of claim 1 wherein said circuitry comprises non-linear and/or active electronic components and wherein said buffer layer covers at least part of said non-linear and/or active electronic components.

20. A method for manufacturing a sensor device having a chip with an integrated sensitive structure and integrated circuitry, and wherein said circuitry comprises semiconductor electronic components, said method comprising the steps of providing a wafer comprising a plurality of chips, integrating, onto a surface of said chips, a buffer layer surrounding said sensitive structure, wherein said buffer layer is structured on said wafer by removing said buffer layer at least partially at a location of said sensitive structure, after structuring said buffer layer, cutting said wafer into said chips, providing a mold defining an interior space and having a section extending into said interior space, placing at least one of said chips in said mold with said section abutting against said buffer layer, introducing a hardening material into said mold for casting a housing over said at least one chip, after hardening said material at least partially, removing said section thereby forming an access opening extending to said sensitive structure, wherein said buffer layer covers at least part of said semiconductor electronic components.

* * * * *